United States Patent
Franceschetti et al.

(10) Patent No.: US 6,607,648 B1
(45) Date of Patent: Aug. 19, 2003

(54) METHOD AND APPARATUS FOR GENERATING AQUEOUS SILICA NETWORK PARTICLES

(75) Inventors: Donald R. Franceschetti, Memphis, TN (US); David R. Kime, deceased, late of Memphis, TN (US), by Margie Kime, legal representative; Stanley E. Stevens, Rosemark, TN (US)

(73) Assignee: Integrity Technologies LLC, Memphis, TN (US)

( * ) Notice: Subject to any disclaimer, the term of this patent is extended or adjusted under 35 U.S.C. 154(b) by 0 days.

(21) Appl. No.: 09/787,217

(22) PCT Filed: Nov. 9, 1999

(86) PCT No.: PCT/US99/26538
§ 371 (c)(1),
(2), (4) Date: Mar. 13, 2001

(87) PCT Pub. No.: WO00/28113
PCT Pub. Date: May 18, 2000

Related U.S. Application Data (60) Provisional application No. 60/107,752, filed on Nov. 10, 1998.

(51) Int. Cl.⁷ .............................. C01B 33/12; B01F 7/16
(52) U.S. Cl. ........................ 204/557; 204/660; 204/664; 366/136; 366/137; 366/282; 424/724
(58) Field of Search .................................. 204/557, 660, 204/664, 155; 366/136, 137, 282, 348; 424/400, 401, 724; 422/186.01

(56) References Cited

U.S. PATENT DOCUMENTS

| | | | |
|---|---|---|---|
| 3,754,734 A | * 8/1973 | Hoyle et al. | 259/4 |
| 4,494,959 A | 1/1985 | Funk | 44/51 |
| 4,888,113 A | 12/1989 | Holcomb | 210/222 |
| 5,012,110 A | 4/1991 | Kropp | 250/492.1 |
| 5,209,646 A | 5/1993 | Smither | 417/50 |
| 5,312,321 A | 5/1994 | Holcomb | 600/9 |
| 5,344,489 A | 9/1994 | Matijevic et al. | 106/442 |
| 5,438,083 A | * 8/1995 | Takimoto et al. | 523/401 |
| RE35,181 E | 3/1996 | Hudz | 261/142 |
| 5,537,363 A | 7/1996 | Holcomb | 366/136 |
| 5,599,531 A | 2/1997 | Holcomb | 424/70.1 |
| 5,607,667 A | 3/1997 | Holcomb | 424/70.1 |
| 5,658,573 A | 8/1997 | Holcomb | 424/400 |
| 5,885,596 A | 3/1999 | Parab | 424/401 |
| 5,939,051 A | 8/1999 | Santalucia et al. | 424/49 |

OTHER PUBLICATIONS

Klaus J. Kronenberg, "Experimental Evidence for Effects of Magnetic Fields on Moving Water," IEEE Tranactions on Magnetics, vol. Mag–21, No. 5, Sep. 1985, pp. 2059–2061.
Abstract of SU 929,589 B (Kharkov Institute of Communal Building Engineering, USSR) May 23, 1982.

* cited by examiner

Primary Examiner—Roy King
Assistant Examiner—William T. Leader
(74) Attorney, Agent, or Firm—Quarles & Brady LLP

(57) ABSTRACT

An aqueous composition including silica particles with a particle size distribution and particle structure that improve the water retention and exchange characteristics of the aqueous composition is provided. The aqueous silica composition includes silica network particles and water. The silica network particles comprise main particles and bridging particles that form chains between adjacent main particles. The main particles have a particle size greater than the particle size of the bridging particles. Because of the presence of the silica network particles, the aqueous composition is capable of wetting a hydrophobic substrate more than pure liquid water. The silica network particles are generated in water by a method in which an aqueous sodium silicate solution is subjected to vigorous agitation in air, followed by periods of circulation through magnetic fields of alternating direction and further periodic agitation exposed to the air. An apparatus for carrying out the method is provided.

29 Claims, 7 Drawing Sheets

METHOD AND APPARATUS FOR GENERATING AQUEOUS SILICA NETWORK PARTICLES

CROSS-REFERENCE TO RELATED APPLICATIONS

This application claims priority from U.S. Provisional Patent Application No. 60/107,752 filed Nov. 10, 1998.

BACKGROUND OF THE INVENTION

The present invention relates to a method and apparatus for forming silica network particles in water using magnetic treatment and the gradual adsorption of carbon dioxide from air, and also relates to an aqueous composition that includes the silica network particles and can be used to hydrate body parts such as skin.

The use of magnetic fields to alter the course of chemical reactions in water has been reported in the scientific literature for some time. For instance, in "Experimental Evidence for Effects of Magnetic Fields on Moving Water," IEEE Transactions on Magnetics, Vol. Mag-21, No. 5, September 1985, pages 2059–2061, Kronenberg reported that passage of a water layer in which a calcium carbonate precipitate was forming altered the crystal form (growth habit) of the precipitate; and in U.S. Pat. No. 4,888,113, there is disclosed a device including bar magnets placed on either side of a pipe, which prevents the formation of carbonate scale in the pipes.

It is also reported in the patent literature that an aqueous colloidal silica can be formed from soluble silicates by repeated passage of the silicate solution through an appropriately structured magnetic field. For example, U.S. Pat. Nos. 5,658,573, 5,607,667, 5,599,531 and 5,537,363 disclose a method and an apparatus for generating a silicate colloid from a highly alkaline and nonstoichiometric solution of sodium silicate using a quadrupole magnetic field. It is reported that the method and apparatus produce particles from 10 to 100 angstroms in size. These patents also report that the silicate colloid produced using the method and apparatus can be used as a hydrating agent in body care and hair care compositions.

Generally, hydrating agents are incorporated into skin care products in order to enable water to penetrate into skin. The skin consists of two layers: the epidermis, the outer layer, and the dermis, the inner layer. The epidermis is a stratified, squamous epithelial layer whose cells undergo a process of division and differentiation. The outermost portion of the epidermis is the keratinized stratum corneum. The keratinization provides mechanical protection and is also a water barrier. Therefore, it not only helps keep the internal milieu constant and prevents water loss, but also prevents easy access to the deeper layers by environmental products. This physical attribute thus makes it difficult to hydrate the inner layer of the skin when it becomes dry. Accordingly, there have been efforts to prepare a hydrating agent that when incorporated into a skin care composition allows the composition to hydrate the skin faster and more easily than bulk water.

Although it is reported in U.S. Pat. Nos. 5,658,573, 5,607,667, 5,599,531 and 5,537,363 that the colloidal silica prepared by the disclosed methods satisfies the need for a hydrating agent that will enable water to penetrate skin, it is believed the colloidal silica disclosed in these patents does not provide an optimum solution to the problem of inadequate hydrating action in skin care products. Specifically, the particle size distribution and the particle structure of the colloidal silica in the aqueous composition in U.S. Pat. Nos. 5,658,573, 5,607,667, 5,599,531 and 5,537,363 significantly limit: (1) the water retention and exchange characteristics of the colloid; (2) the extent of interaction of absorbed water on the colloidal silica; (3) the interaction of an aqueous composition including the colloid with a hydrophobic substrate; and (4) the wetting properties of an aqueous composition including the colloid on a hydrophobic substrate.

Accordingly, there is a need for an silica composition with a particle size distribution and particle structure that improves the water retention and exchange characteristics of an aqueous composition including the silica composition. In addition, there is a need for an aqueous silica composition that has improved wetting characteristics when interacting with a hydrophobic substrate.

BRIEF SUMMARY OF THE INVENTION

The foregoing needs are satisfied by aqueous silica network particles with unusual water retention and exchange properties. The silica network particles are generated in water by a method in which an aqueous sodium silicate solution is subjected to vigorous agitation in air, followed by periods of circulation through magnetic fields of alternating direction and further periodic agitation exposed to the air. The incorporation of carbon dioxide from the air occurs in both stages of agitation in this process. The result, at the end of the method, is aqueous silica particles with unique network morphology. The term "network" as used herein describes a morphology wherein bridging particles form chains between main particles. This network morphology can also be described as a three dimensional mesh-like structure. With this network morphology, fluid regions are contained within the network. In one version of the invention, the aqueous silica network particles have a structure comprising bridging particles that form chains between adjacent main particles, wherein the main particles have a particle size greater than the bridging particles. An aqueous composition having the silica network particles has a lower interaction energy with hydrophobic materials than bulk water, and when added to a typical skin care preparation, enhances the exchange of water with the layers of skin.

Without intending to be bound by theory, it is believed that when the silica network particles are present in an aqueous composition, the network of each particle surrounds and encloses layers of bound water with a structure appreciably different from that of bulk water. It is believed that the alternating magnetic field used in generating the silica network particles serves to change the rate at which stable aggregates of water molecules form around other molecules or ions, which in turn alters the aggregation kinetics of the silica to produce the network particle morphology. In the normal polymerization of silicate solutions, a variety of particle sizes are formed, but a form of Ostwald ripening predominates wherein bigger particles grow at the expense of smaller particles. In contrast, the silica in the present invention forms the aforementioned network particle structure. It is further believed that the unusual properties of the silica network particles of the present invention are due to the gradual lowering of pH as carbon dioxide is absorbed, favoring chain formation over particle growth, and the stabilization of water clathrate-like structures around molecular carbon dioxide that absorb on the surface of larger but not smaller particles favoring the formation of chains of smaller particles. The result is silica network particles in water with an unusual physical reactivity to liquid water.

An aqueous composition of the silica network particles can be beneficially used as a hydrating agent in a wide variety of body care compositions, such as shampoos, conditioners, styling gels, styling mists, hair coloring preparations, body lotions, face creams, skin creams, bath additives, pedicure and manicure applications, hand lotions, lip balms, mouthwashes, toothpaste, lipsticks, suntan lotions, and sunscreen lotions. The use of an aqueous composition including the silica network particles in facial cleansers, moisturizing creams, and facial mists provides a package for improvement of skin and mucus membrane moisture, tone, and youthful appearance.

It is therefore an object of the present invention to provide an aqueous composition including silica particles that have a particle size distribution and particle structure that improve the water retention and exchange characteristics of an aqueous composition including the silica particles.

It is another object of the present invention to provide an aqueous silica composition that has improved wetting characteristics when interacting with a hydrophobic substrate.

It is a further object of the present invention to provide a body care composition that has improved hydration characteristics when compared to known body care compositions.

It is still another object of the present invention to provide a method for forming an aqueous composition including silica particles that have a particle size distribution and particle structure that improve the water retention and exchange characteristics of an aqueous composition including the silica particles.

It is yet another object of the present invention to provide an apparatus for forming an aqueous composition including silica particles that have a particle size distribution and particle structure that improve the water retention and exchange characteristics of an aqueous composition including the silica particles.

These and other objects, advantages and aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefore, to the claims herein for interpreting the scope of the invention.

DETAILED DESCRIPTION OF THE INVENTION

An aqueous silica composition in accordance with the present invention includes silica network particles and water. The silica network particles comprise main particles and bridging particles that form chains between adjacent main particles. The main particles have a particle size greater than the particle size of the bridging particles. Preferably, the silica network particles have a particle diameter greater than or equal to 1000 nanometers, and most preferably, the silica network particles have a particle diameter greater than or equal to 3000 nanometers. The silica network particles are heterodisperse as determined by zeta potential measurements. Preferably, the main particles and the bridging particles have a substantially spheroid shape, and form a three dimensional structure. Preferably, the aqueous silica composition has a carbonate concentration (carbonic acid plus bicarbonate ion plus carbonate ion) of about 4 to about 8 millimoles per liter after preparation. The aqueous silica composition is capable of wetting a hydrophobic substrate more than pure liquid water.

The aqueous silica network particles of the present invention are prepared by dissolving sodium metasilicate pentahydrate ($Na_2SiO_3 \cdot 5H_2O$) in distilled water in an open-air mixing chamber to produce a solution. The solution is then subjected to constant agitation by an agitator. Preferably, the amount of sodium metasilicate pentahydrate added to the water is such as to prepare a solution having about 100 parts per million to about 500 parts per million, and preferably 300 parts per million, in silica before any further processing. No further dilution of the silicate solution is required. The silicate/water mixture is agitated while exposed to the open air at room temperature for a period of time. The agitation results in the formation of some sodium carbonate and sodium bicarbonate through absorption of carbon dioxide from the air. The pH of the solution after the initial agitation (which will often be referred to hereinafter as "Stage 1 Material") is preferably about 9.5 to about 10.5.

The solution ("Stage 1 Material") is then pumped repeatedly through nonmagnetic helical tubing which passes repeatedly past the pole faces of magnets arranged so that the South and North pole faces alternate in succession so that the solution experiences a repeated change in field direction. After passing through the tubing, the solution passes into a mixing vessel where it is subjected to further agitation in contact with air. The solution is repeatedly recirculated through the tubing and the mixing vessel. After processing, the solution (which will often be referred to hereinafter as "Stage 2 Material") is removed and stored in non-glass containers. The pH of the Stage 2 Material after processing is preferably about 8.5 to about 9.5.

A solution treatment apparatus 10 which has been found advantageous for preparing the aqueous silica network particles of the present invention is shown in FIGS. 1–5. As shown, an open-air mixing vessel 12 is secured to a frame 14. A variable speed electric motor 15, which is capable of operating at speeds of 1750–2500 rpm, is also secured to the frame 14. A shaft 16 extends from the motor 15 to support a 2 inch serrated cowl's shearing blade 17 in the mixing vessel 12. The mixing vessel 12 and the motor 15 are positioned such that a solution in the mixing vessel 12 is subject to agitation by the shearing blade 17 off the central vertical axis of the mixing vessel 12.

Figure 1:
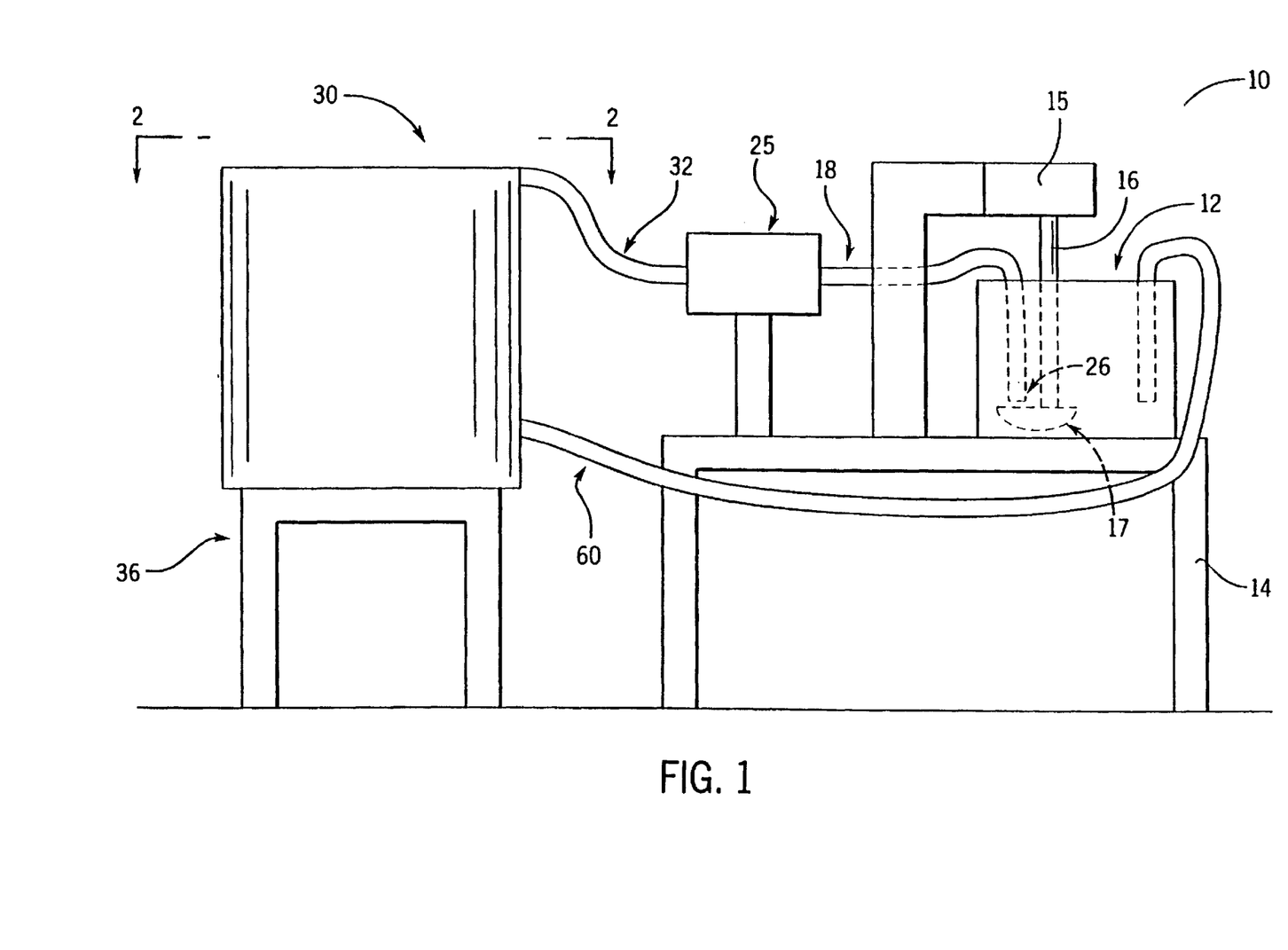
FIG. 1 is a side view of an apparatus in accordance with the present invention for preparing the aqueous silica network particles of the present invention.

A positive displacement pump 25 is also secured to the frame 14. The pump 25 is fully adjustable so that a desired volume flow rate and pump pressure can be achieved. The inlet of the pump 25 is placed in fluid communication with the mixing vessel 12 by way of a vessel output conduit 18. The vessel output conduit 18 is preferably a non-magnetic stainless steel tube. An inlet 26 of the vessel output conduit 18 is accurately positioned in the mixing vessel 12 such that only adequately aerated solution is drawn into the pump 25. The outlet of the pump 25 is placed in fluid communication with a magnetic field generating unit, indicated generally at 30, by way of a pump output conduit 32.

Figure 2:
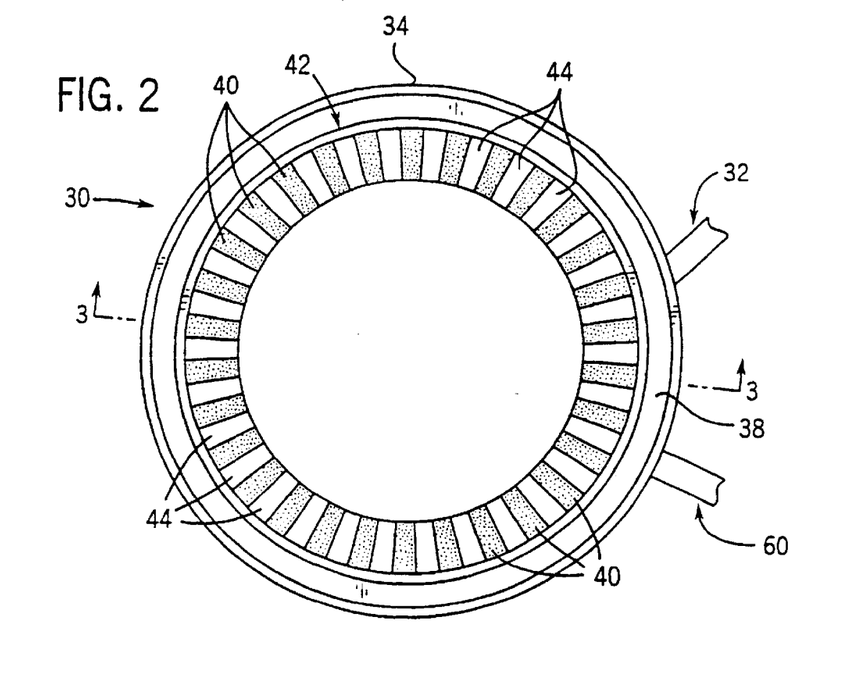
FIG. 2 is a top view of the magnetic generating unit of the apparatus of the present invention taken along line 2—2 of FIG. 1.
Figure 3:
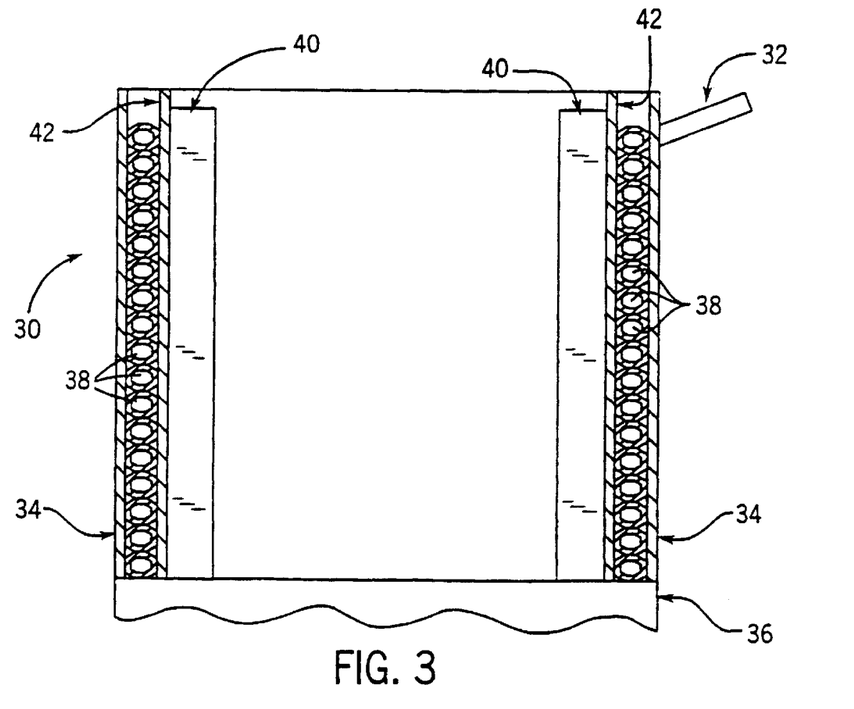
FIG. 3 is a cross-sectional view of the magnetic generating unit shown in FIG. 2 taken along line 3—3 of FIG. 2.

The magnetic field generating unit 30, best shown in FIGS. 2 and 3, is a freestanding unit that allows a solution to repeatedly pass through an alternating magnetic field. The magnetic field generating unit 30 includes an outer cylindrical carbon steel tubular wall 34 which is mounted on a frame 36. The tubular wall 34 is preferably made from a sheet of ferromagnetic material to add an additional magnetic image field to the magnetic field generating unit 30. Fluorocarbon lined non-magnetic tubing 38 is wrapped into a helical coil along the inner surface of the tubular wall 34. The tubing 38 extends from a top portion of the tubular wall 34 to a bottom portion of the tubular wall 34. Preferably, the tubing 38 is a non-ferrous tubing sold under the trademark "Tygon" by Dupont, Dover, Del., USA. In one version of the magnetic generating unit 30, the tubing 38 is approximately fifty feet long and has a ½ inch inside diameter. The solution to be treated is received by the tubing 38 by way of the pump output conduit 32 which is in fluid communication with the pump 25.

The magnetic field generating unit 30 also includes vertical columns of evenly spaced magnets 40 that are positioned inside an inner cylindrical drum 42 made from iron or other ferromagnetic material to take advantage of a magnetic image field which adds to the magnetic field intensity. The inner cylindrical drum 42 is positioned inside the helical coiled tubing 38. The magnets 40 are held in position by the inner drum 42 and are separated from each other by vertical foam non-magnetic insulation columns 44. The magnets 40 are arranged such that the poles of adjacent magnets are of opposite orientation, i.e., the North ("+") pole of one magnet faces the tubing 38 and the South ("−") pole of the adjacent two magnets faces the tubing 38. In a preferred version of the magnetic generating unit 30, the pole faces of the magnets 40 arranged so that the South and the North pole faces alternate in succession with approximately 1 inch between centers.

With this arrangement of the magnets 40, the solution moving through the tubing 38 experiences a constantly changing magnetic field every inch while in the magnetic field generating unit 30. As particles in a solution flow through the tubing 38, they cut through the lines of magnetic flux of the magnetic field generated by the magnets 40, i.e., the direction of fluid flow through the tubing 38 is at right angles to the magnetic field.direction. It is preferred that all of the magnets 40 be identical, except for their pole orientation, and that they each produce approximately equal magnetic flux. Preferably, the magnetic field strength is approximately 1,000 Gauss (0.1 Tesla) at the pole face of the individual magnets 40 and the magnetic field is calculated to remain stronger than 500 Gauss throughout the ferromagnetic enclosed configuration of the magnetic generating unit 30. Preferably, the magnets 40 are permanent magnets. Alternatively, the magnets 40 may be electromagnets powered by a D.C. power supply. Further, paramagnetic ions be added to enhance the formation of the material.

Figure 4:
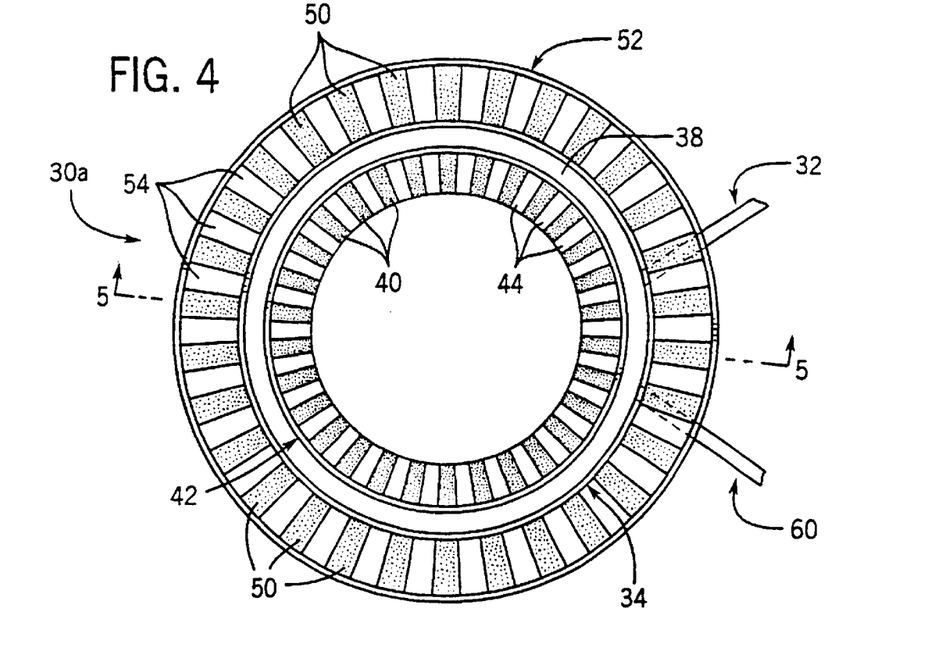
FIG. 4 is a top view of an alternative magnetic generating unit of the apparatus of the present invention taken along line 2—2 of FIG. 1.
Figure 5:
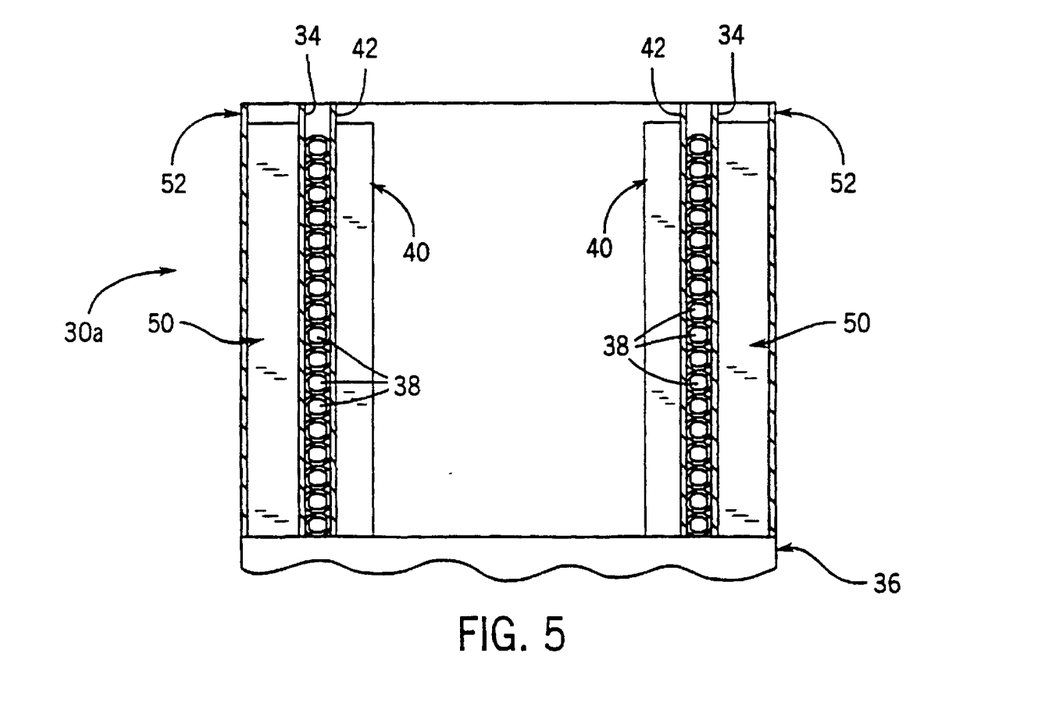
FIG. 5 is a cross-sectional view of the magnetic generating unit shown in FIG. 4 taken along line 5—5 of FIG. 4.

In another version of the invention, the solution treatment apparatus 10 has an magnetic field generating unit 30a, shown in FIGS. 4 and 5, that includes a second group of vertical columns of evenly spaced magnets 50 that are positioned outside the tubular wall 34. The magnets 50 are positioned inside an outer cylindrical drum 52 made from iron or other ferromagnetic material to take advantage of a magnetic image field which adds to the magnetic field intensity. The outer cylindrical drum 52 and the magnets 50 are positioned outside the tubular wall 34 and the helical coiled tubing 38. The magnets 50 are held in position by the outer drum 52 and are separated from each other by vertical non-magnetic insulation columns 54. The magnets 50 are arranged such that the poles of adjacent magnets are of opposite orientation, i.e., the North ("+") pole of one magnet faces the tubing 38 and the South ("−") pole of the adjacent two magnets faces the tubing 38.

The solution treatment apparatus 10 can be used to treat a solution as follows. A solution to be treated is added to the open-air mixing vessel 12. The variable speed electric motor 15 is activated and preferably is set to operate at a speed of 1750–2500 rpm. The solution in the mixing vessel 12 is then subject to agitation by the shearing blade 17 at a position off the central vertical axis of the mixing vessel 12. After sufficient agitation and aeration of the solution, the pump 25 pumps the solution from the mixing vessel 12 by way of the vessel output conduit 18. As noted above, the inlet 26 of the vessel output conduit 18 is accurately positioned in the mixing vessel 12 such that only adequately aerated solution is drawn into the pump 25. The pump 25 pumps the solution through the pump output conduit 32 and into the helical coiled tubing 38 in the magnetic field generating unit 30. After the solution to be treated has circulated through the tubing 38 in the magnetic generating unit 30, it is then returned to the mixing vessel 12 by way of a magnetic generating unit output conduit 60 which is in fluid communication with the tubing 38 and the mixing vessel 12. In the mixing vessel 12, the solution is again subjected to agitation and aeration by the shearing blade 17, and the circulation process occurs again, i.e., the solution is pumped from the mixing vessel 12, through the tubing 38 in the magnetic generating unit 30 and returned to the mixing vessel 12. The recirculation through the mixing vessel 12 and the tubing 38 is repeated for a predetermined time period, after which the pump 25 and the motor 15 are turned off and the treated solution is removed from the mixing vessel 12.

Improved body care compositions can be formulated by adding an aqueous composition including the aqueous silica network particles of the present invention to an existing body care composition such as a skin cream, body lotion, shampoo, hair conditioner, cleanser, etc. to bring the concentration of the silica network particles within the body care composition to a preferred range of from about 1 parts per million to about 50 parts per million. The body care composition is then used in a normal manner. The presence of the silica network particles of the present invention in the body care composition increases the ability of the composition to penetrate into body parts. When incorporating the aqueous silica network particles into skin care products, it is believed that the presence of aqueous silica network particles allows the water in the product to penetrate more deeply into the deeper layers of the epidermis.

The invention is illustrated further in the following Examples which are exemplary in nature and are not intended to be limiting.

EXAMPLE 1

Silica network particles in water in accordance with the present invention were prepared as follows. A 45.6 gram sample of commercial grade sodium metasilicate pentahydrate ($Na_2SiO_2.5H_2O$, available from Sigma Chemical, St. Louis, Mo., USA) was dissolved in 15 gallons (56,700 grams) of distilled water in a non-metallic, thirty-gallon container with a conical bottom at a room temperature of approximately 20 degrees Celsius. The sodium metasilicate solution was then placed in a thirty-gallon polyethylene, cylindrical tank having a diameter of 18 inches and a depth of 35 inches. The solution was then mixed with a stainless steel dispersion blade having a diameter of 6 inches. The dispersion blade was designed to shear the solution by incorporating large multi-it angled "teeth" in its design. The blade was mounted on an axis approximately 10 degrees from the tank centerline, which served to increase the shearing action of the blade. A 0.5 inch diameter stainless steel shaft was used to attach the blade to a 1.5 horsepower, variable speed electric motor which rotated the blade at an average speed of between 1750 and 2500 rpm. The solution was agitated using the dispersion blade for 2½ hours. At the end of the agitation time, the pH of the solution (Stage 1 Material) as measured with a calibrated glass pH electrode (available from Fisher Scientific, Philadelphia, Penn., USA) was 9.5–10.5.

The Stage 1 Material was then removed from the thirty-gallon container after processing and one gallon of the Stage 1 Material was added to the mixing vessel 12 of the solution treatment apparatus 10 described above. The solution was agitated and aerated in the mixing vessel 12 and pumped through approximately fifty feet of ½ inch inside diameter "Tygon" brand tubing that coiled around vertical columns of evenly spaced magnets as described above in the description of the solution treatment apparatus 10. The pump rate and quantity of Stage 1 Material was selected such that in four hours of operation of the pump and the motor of the solution treatment apparatus, the Stage 1 Material passed 360 times through the tubing. After processing, the solution (the "Stage 2 Material") is removed and stored in a non-glass containers. The pH of the Stage 2 Material was determined to be 8.5–9.5 as measured with a calibrated glass pH electrode. It was colorless and free of visible particulate matter and had an electrical conductivity between 0.65 and 0.75 mS/cm. The Stage 2 Material is completely miscible in water, ethanol, methanol, isopropanol, and acetonitrile.

Analysis of the Aqueous Silica Network Particles Prepared in Example 1 a. Light Scattering Analysis

In order to determine the structure and the particle size distribution of the aqueous silica network particles prepared in Example 1, samples of the material prepared in Example 1 were analyzed using a light scattering apparatus. Specifically, light scattering studies were conducted using a Coulter-Beckman DELSA 440 apparatus, which allows measurements to be made in two different modes: a size determination mode and a zeta-potential/electrical mobility mode. This particular apparatus works by analyzing light scattered from four sub-beams of an original helium-neon laser beam, sent at different angles through the material to be studied. To avoid multiple scattering effects, the beam geometry is such that the scattering volume is small, from 0.01 to 0.03 microliters.

Samples of the material prepared in Example 1 were analyzed using the size determination mode of the light scattering apparatus. A majority of the analyses using the size determination mode indicated particle sizes in excess of 3000 nanometers. Scattering by smaller particles appeared only in a fraction of the measurements made with the instrument. Specifically, 85 percent of the size determination runs showed particles of size greater than 3000 nanometers.

Samples of the material prepared in Example 1 were then analyzed using the zeta-potential/electrical mobility mode of the light scattering apparatus. When using the zeta-potential/electrical mobility mode, a homodisperse material typically generates experimental data showing a single value of the zeta potential. However, when samples of the material prepared in Example 1 were analyzed using the zeta-potential/electrical mobility mode of the light scattering apparatus, several groupings of zeta potential measurements occurred at roughly −12, −25 and −39 mV. After ten repetitions of the zeta potential measurement on at least two samples of the material prepared in Example 1, more than 50% of the samplings showed a zeta-potential value more negative than −10 mV. Therefore, it can be concluded that the material prepared in Example 1 was heterodisperse. Upon plotting of the half width of the observed peaks against scattering angle, it was confirmed the material prepared in Example 1 was heterodisperse.

b. Electron Microscopy Analysis

In order to determine the structure and the particle size distribution of the aqueous silica network particles prepared in Example 1, samples of the material prepared in Example 1 were analyzed using Transmission Electron Microscopy and Environmental Scanning Electron Microscopy.

First, Transmission Electron Microscopy (TEM) was used to characterize the particle size distribution of: (1) a sample of the silica network particles of Example 1 after the initial agitation step (Stage 1 Material), and (2) a sample of the silica network particles in water of Example 1 after complete processing in accordance with the methods and apparatus of Example 1 (Stage 2 Material). It was determined that the particle size distribution differed between Stage 1 Material and Stage 2 Material, when dried completely under vacuum. Unexpectedly, the viewing of all these micrographs suggested a ramifying, beads on a string model, for the structure of the Stage 2 material. In other words, the silica network particle structure comprised bridging particles that formed chains between adjacent main particles, and the main particles had a particle size greater than the bridging particles. Many of the micrographs of the Stage 2 material suggested a superstructure of these ramifying beads-on-a-string resembling a collapsed three-dimensional ball of chicken wire. Smaller versions of this structure were seen on micrographs of the Stage 1 material.

Second, Environmental Scanning Electron Microscopy (ESEM) was used to further determine the structure and the particle size distribution of the aqueous silica network particles prepared in Example 1. ESEM has proven to be quite advantageous in certain materials characterization analyzes as the material being analyzed can be viewed directly in its native state. For instance, in ESEM, no sample preparation is needed (although the atmosphere within the sample chamber must be controlled) and water does not have to be excluded from the materials sample being analyzed. A sample in its native state is placed on the sample stage in the vacuum chamber of an ESEM. The chamber is slowly evacuated while maintaining a water vapor pressure of about 6.6 torr and 100% relative humidity in the chamber. Samples can be allowed to dry down by evaporation of the water in the sample.

Figure 6A:
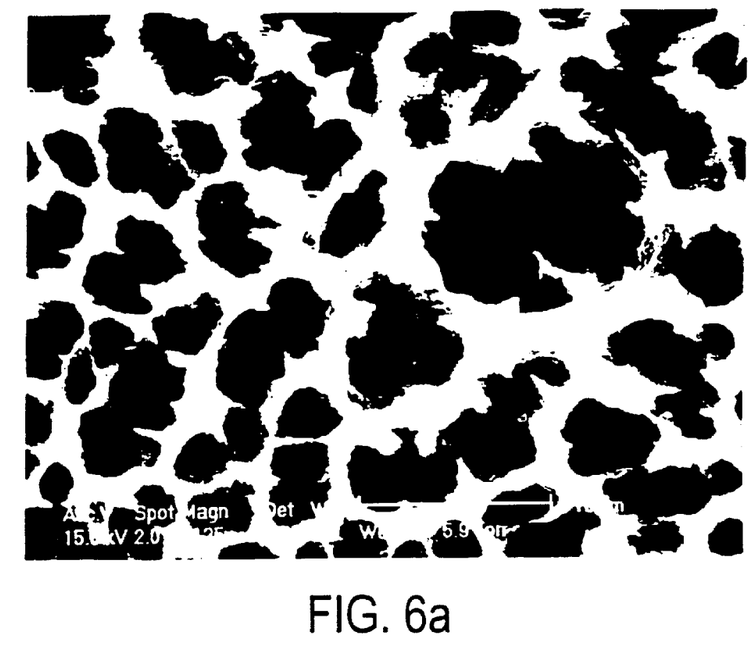
FIG. 6a is a photomicrograph taken with an Environmental Scanning Electron Microscope at a magnification of 3125× of a silica network particle after a first stage of processing in accordance with the present invention.
Figure 6B:
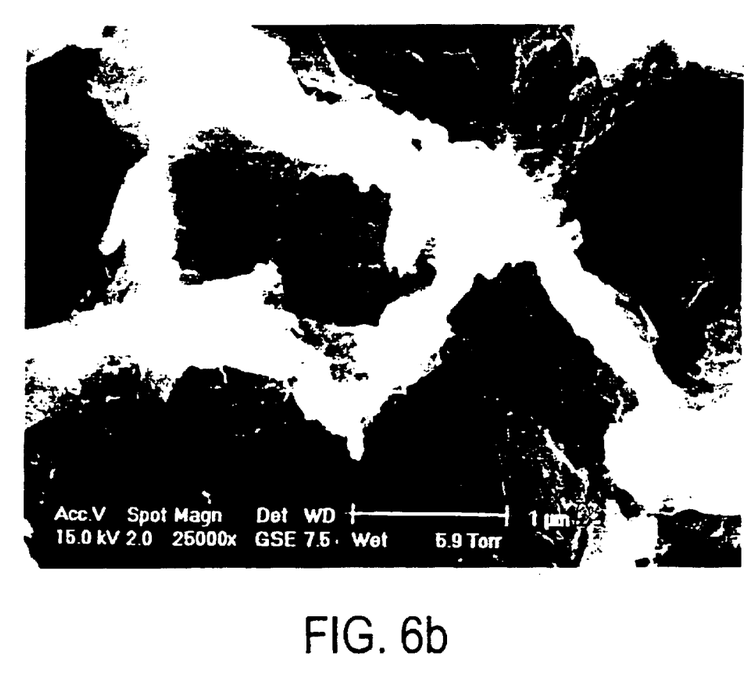
FIG. 6b is a photomicrograph taken with an Environmental Scanning Electron Microscope at a magnification of 25000× of a silica network particle after a first stage of processing in accordance with the present invention.

The above ESEM procedure was applied to a sample of Stage 1 Material in its native state. The structure observed was when the water present in its native state vaporized. As seen in FIGS. 6a and 6b, the structure observed consisted of stacks of many small plates that ramify throughout the sample. Multiple sharp points were exhibited in this structure which is consistent with an underlying tetrahedral base unit for the material. A multitude of jumbled stacked plates were evident in higher magnification views, which is suggestive of the structure of graphite, although the Stage 1 material was much more irregular than graphite.

Figure 7:
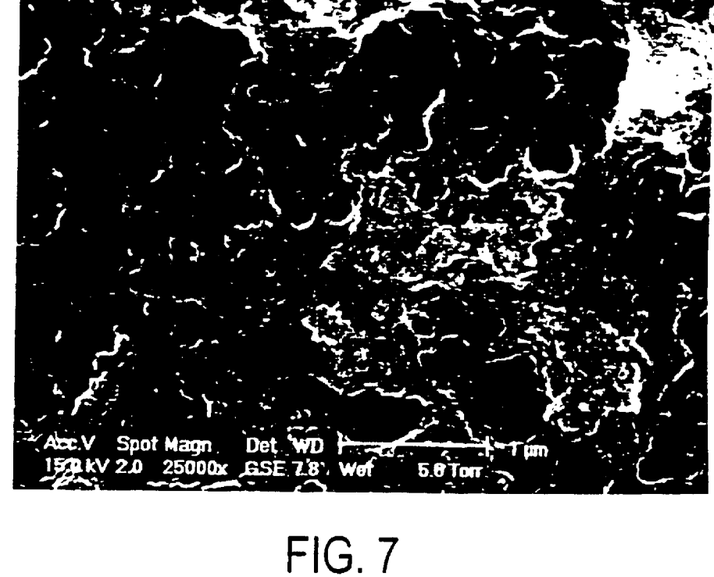
FIG. 7 is a photomicrograph taken with an Environmental Scanning Electron Microscope at a magnification of 25000× of a silica network particle after complete processing in accordance with the present invention.
Figure 8:
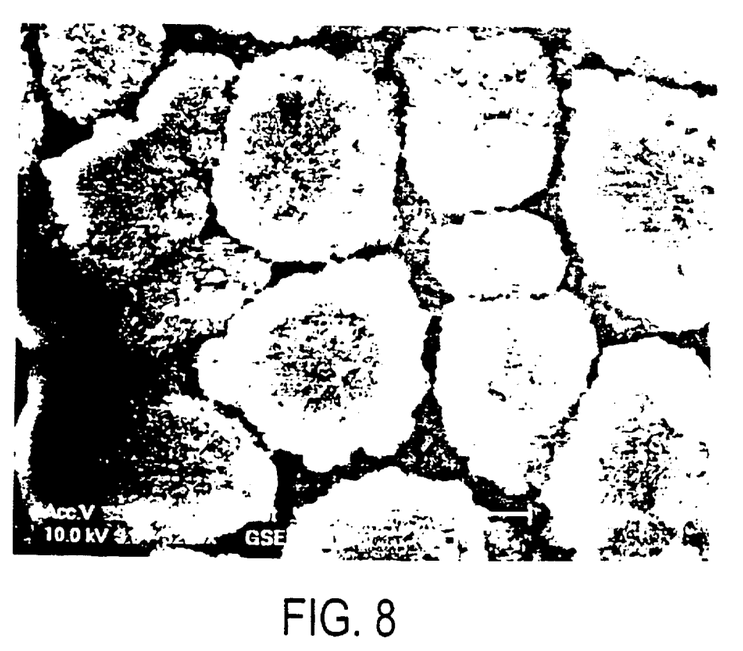
FIG. 8 is a photomicrograph taken with an Environmental Scanning Electron Microscope at a magnification of 3200× of a silica network particle after complete processing in accordance with the present invention.

When identical ESEM processing was used with the Stage 2 Material in its native state, a very different structure was revealed and is shown in FIGS. 7 and 8. As in the Stage 1 Material, there was observed a ramifying interconnected structure. However, the Stage 2 Material is composed of a multitude of irregular spheroids joined to each other. The Stage 2 Material also has rounded soft edges and appears like a berry pudding as best seen in FIG. 8.

During the initial drying down of the Stage 2 material in the ESEM chamber, crystals, presumably of a carbonate, formed evanescently on the surface of the silica network. In fact, at the drying front of a drop of the Stage 2 Material, lower magnification revealed extensive carbonate crystals appearing through a water film (the ESEM visualizes water as essentially opaque) obscuring the structure of the Stage 2 Material (See FIG. 8.). These carbonate structures were 6–10 micrometers in diameter.

When the relative humidity of the ESEM sample chamber was reduced to below about 30%, the Stage 1 Material dried in about two minutes. When the same reduction in relative humidity was done with Stage 2 Material, it took about 30 minutes to dry. Clearly, the water retaining capacity of Stage 2 Material was remarkably better than for the Stage 1 Material. In other words, the water retaining capacity of the Stage 2 Material, which was treated in the magnetic field, was improved in relation to the Stage 1 Material, which was not treated in the magnetic field.

Third, another ESEM procedure was used to further determine the structure and the particle size distribution of the aqueous silica network prepared in Example 1. In this procedure, samples prepared in Example 1 were analyzed using analysis technology that involved the freezing of samples at the temperature of liquid nitrogen and the transfer of these samples to a sample stage that maintained the samples at the temperature of liquid nitrogen and then allowed for the controlled warming of the sample stage. After processing, samples in their frozen native state were allowed to warm slowly to about the temperature of dry ice. The procedure allowed the observer to continuously monitor what happened on the sample stage during the slow warming process. In effect, the sample was allowed to self-etch during the warming period revealing the structure within the frozen water matrix.

Figure 9:
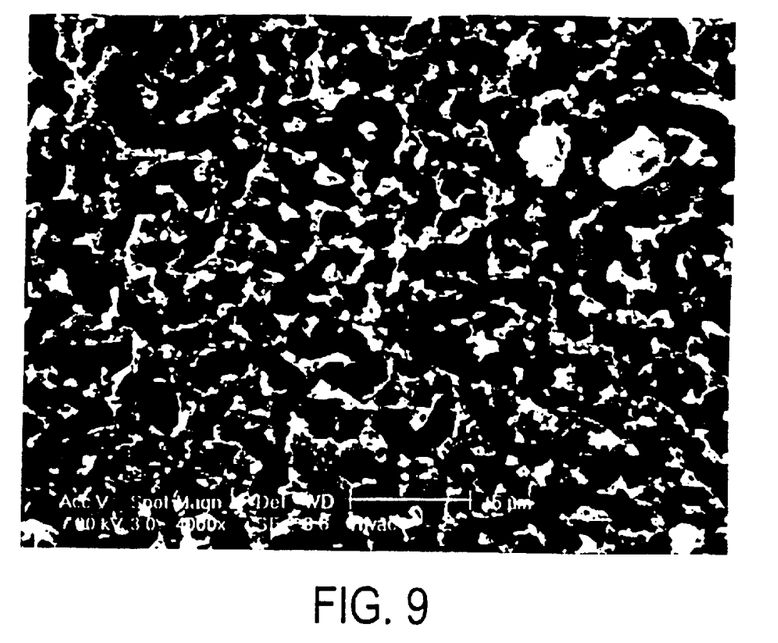
FIG. 9 is a photomicrograph taken with an Environmental Scanning Electron Microscope at a magnification of 4000× of a silica network particle after complete processing in accordance with the present invention and after freezing the particle with liquid nitrogen.
Figure 10:
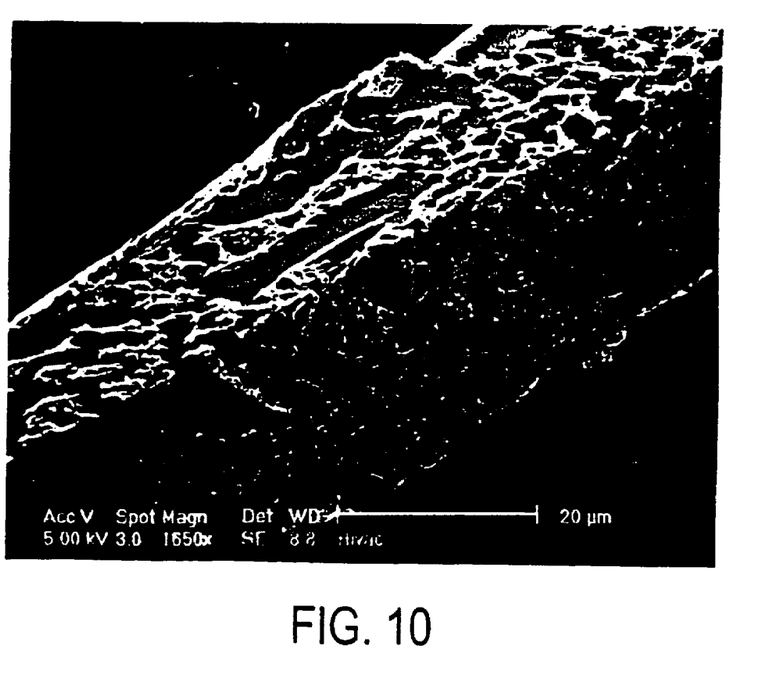
FIG. 10 is a photomicrograph taken with an Environmental Scanning Electron Microscope at a magnification of 1650× of a silica network particle after complete processing in accordance with the present invention and after freezing the particle with liquid nitrogen.
Figure 11:
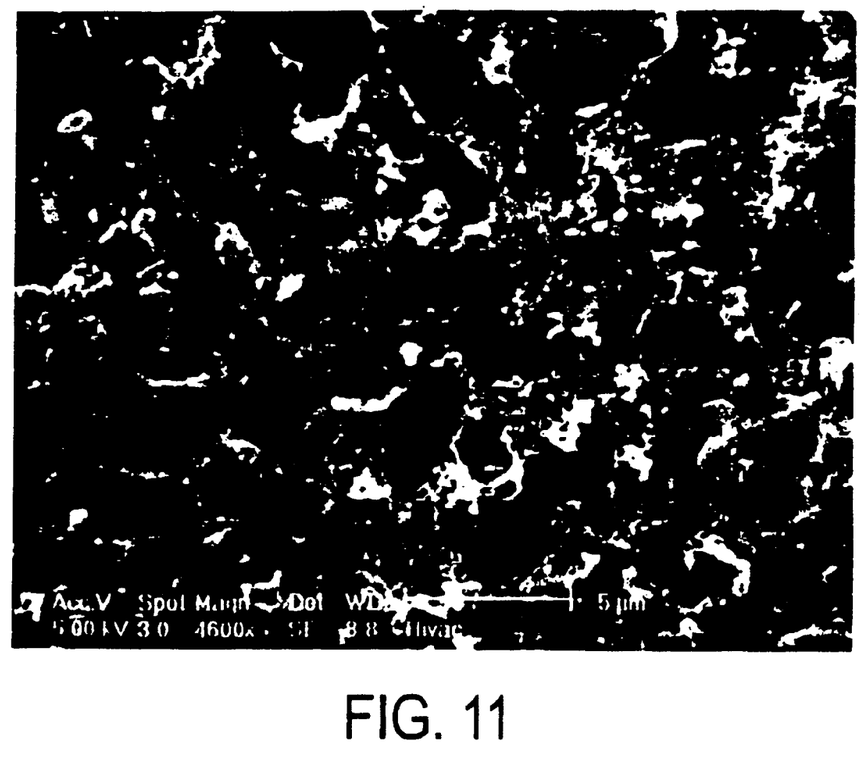
FIG. 11 is a photomicrograph taken with an Environmental Scanning Electron Microscope at a magnification of 4600× of a silica network particle after complete processing in accordance with the present invention and after freezing the particle with liquid nitrogen.

Using this ESEM technique, the Stage 1 Material was revealed to have a complex ramifying structure. As in the unfrozen sample of Stage 1 material previously discussed, the structure consisted of many jumbled stacks of plates with sharp edges fused together in a ramifying array. In contrast, the Stage 2 Material as shown in FIGS. 9, 10 and 11, revealed as a complex ramifying system of apparent strings. The material clearly ramifies in three-dimensions as shown in FIG. 10. At higher magnification levels as in FIG. 11, these strings appeared to be made of very small bead-like units fused together to form a complex array of strings.

c. Contact Angle Analysis

In order to determine the extent to which the aqueous silica network particles of the present invention act as a wetting agent (i.e., a surface-active agent that, when added to water, causes it to penetrate more easily, or to spread over the surface of, another material), a contact angle analysis was performed on the aqueous composition including silica network particles prepared in Example 1. Contact angle measurements were taken using a "Tantec" brand Model CAM-PLUS contact angle meter for distilled water (a control), freshly dissolved sodium metasilicate (another control), a sample of the silica solution of Example 1 after the initial agitation step (Stage 1 Material), and a sample of the silica network particles in water of Example 1 after complete processing in accordance with the methods and apparatus of Example 1 (Stage 2 Material). Contact angle measurements for these four materials were taken on: (1) glass, (2) Parafilm® brand moisture proof, self-sealing wrapper material commonly used in chemical laboratories, and (3) Teflon® brand tetrafluoroethylene film. The results are given below in Table 1.

TABLE 1

Contact Angle Measurements (in degrees)

Materials Tested

| Substrate | Water | Sodium Metasilicate Solution | Stage 1 Material (Example 1) | Stage 2 Material (Example 1) |
| --- | --- | --- | --- | --- |
| Glass | 24.5 | 21.1 | 26.8 | 25.4 |
| Parafilm ® film | 99.1 | 99.4 | 100.8 | 95.4 |
| Teflon ® film | 104.6 | 103.5 | 103.2 | 98.8 |

Looking at the results of the contact angle measurements in Table 1, it can be seen that the contact angle for sodium metasilicate solution on glass is somewhat lower than that for distilled water, but, that for both Stage 1 Material and Stage 2 Material, the contact angle is greater than that for distilled water. On the other hand, the contact angle as measured on Parafilm® brand film and Teflon® brand film, which are both highly hydrophobic substrates, is significantly reduced for the Stage 2 Material. These observations are consistent with the notion that the absorbed water on the silica network particles has a modified structure that interacts more favorably with a hydrophobic substrate than that of bulk distilled water.

If the liquid-vapor surface tension of a liquid is known, and its contact angle with a solid is measured, then the solid-vapor and solid-liquid surface tension can be computed using the equations of state devised by Newman, et al. (see *Separation and Purification Methods*, 9, 69–183, 1980 and *J. Colloid. Interface Sci.*, 49, 291, 1974) and known to those skilled in the art. Using the results of the contact angle measurements reported in Table 1, surface tension computations were made and are reported in Table 2 below.

TABLE 2

| | Surface Tension (in mN/m) | | | |
|---|---|---|---|---|
| | | Materials Tested | | |
| Substrate | Water | Sodium Metasilicate Solution | Stage 1 Material (Example 1) | Stage 2 Material (Example 1) |
| Glass | 66.1 | 67.5 | 65.1 | 65.7 |
| Parafilm ® film | 22.9 | 22.6 | 21.7 | 26.1 |
| Teflon ® film | 19.4 | 20.1 | 20.3 | 23.0 |

For a composite material, the liquid vapor surface tension is somewhat time dependent. Assuming a surface tension equal to that of water yields the solid-vapor and solid-liquid surface tensions reported in Table 2, it is noteworthy that the solid-vapor tension, or equivalently, the specific interfacial energy is about 10% reduced for the Stage 2 Material on Teflon® brand film, again indicating a more favorable interaction with a hydrophobic substrate.

d. Titration

It was contemplated that the gradual dissolution and chemical reaction of the sodium metasilicate solution with the carbon dioxide in air is an important step in the formation of the silica network particles of the present invention. In order to determine the extent to which the carbonates are incorporated into the aqueous silica network particles of the present invention, a titration analysis was performed on the aqueous silica network particles prepared in Example 1. An algorithm was developed to fit the titration curve of a 10 milliliter sample of the aqueous silica network particles diluted with an equal amount of water to a theoretical expression based on the published ionization constants of silicic acid $Si(OH)_4$ ($K_1=2\times10^{-10}$, $K_2=K_3=K_4=2\times10^{-12}$) and carbonic acid ($K_1=3\times10^{-7}$, $K_2=5.86\times10^{-11}$). As a result, it was possible to fit the titration data for the aqueous silica network particles prepared in Example 1 with a standard deviation of less than 0.2 milliliters. When the aqueous compositions including silica network particles prepared in Example 1 was titrated with 0.01N HCl and the best fit parameters, a total carbonate (carbonic acid plus bicarbonate ion plus carbonate ion) concentration of between 5.5 and 7.2 millimoles per liter was determined.

EXAMPLE 2

An aqueous composition including silica network particles prepared in accordance with Example 1 was incorporated into cosmetic formulations. The product was tested in three variations, in double-blinded studies. The only difference in the tested variations was the presence or absence of the aqueous composition of the present invention. The objective was to determine if the aqueous composition including silica network particles improved the hydration of the skin, decreased fine wrinkle lines, and enhanced skin tone. The study population age range was 20–65.

The three formulations were sent to 8 cities in the United States to see how well the formulations performed in the various climates and subject to a variety of different environmental factors. A number of different cities were chosen because cosmetic and especially skin care products do not perform equally well in different climates or where different types of tap water are used. The eight cities were Philadelphia, Portland, Houston. Omaha, Atlanta, Los Angeles, San Diego and Memphis. Salons were selected in these cities to conduct these clinical trials based on their background in product development and comparison testing. A total of 1500 participants were tested in the eight cities listed and 1372 of the participants completed evaluations (91%). Side by side comparisons with ½ of the subject's face treated with a typical product and ½ with a product incorporating the aqueous composition of the present invention. The products were prepared as a cleanser, hydrating mist, hydrating gel, surface active cream, and lotion. A pre-interview and a post-interview were conducted with each participant, and the interviews included the following questions: (1) Do you see different results in the hydration of your skin—if so, what?; (2) Is this product better than, or as good as, what you are currently using?; (3) What results appear to be specific to our formulation?; (4) Would you buy this product?; and (5) Did you experience greater hydration, and if so, how long did it seem to last?. After three months, the data from the study were collated, and it was determined that: (1) 83% of subjects liked our formulation better than or as well as what they had been using; (2) 12% of subjects did not like our formulation; (3) 5% of subjects did not have an opinion; and (4) 71% of subjects thought they saw fewer fine lines and wrinkles and better skin tone after using the cosmetic formulation having the aqueous composition including silica network particles prepared in accordance with Example 1.

Clearly, when the aqueous composition including silica network particles of the present invention is applied in combination with standard cosmetic ingredients, the result is an increased moisturization of the skin. When the aqueous composition including silica network particles of the present invention is utilized as a hydrating agent with additional cosmetic agents, results show a very high acceptance rate and preference by men and women.

EXAMPLE 3

When certain participants in the study described in Example 2 reported rapid relief from minor burns (e.g., sunburn) and irritation (e.g., from hot peppers), a systematic study was conducted on the use of certain formulations incorporating the aqueous composition of the present invention on individuals recovering from severe burns and surgical procedures. The studies in burn patients were undertaken to see if the product in the form of a hydrating gel or mist could decrease itching in healed areas of partial thickness injury or healed grafted regions. These areas often show dryness that tends to clinically correlate with their pruritus. Hydrating agents have been used topically to help decrease the itching. The multi-center Institutional Review Board approved study collected twenty evaluable patients, sixteen of these felt the product alleviated itching and hydrated their skin better than a widely used mineral oil based topical agent.

EXAMPLE 4

Patients who undergo laser resurfacing of their skin often experience prolonged redness that decreases the acceptance of the resurfacing. Topical vitamin C has been shown to help decrease this redness postoperatively, but is usually painful on application. In order to determine if the aqueous composition including silica network particles of the present invention can reduce the discomfort of individuals undergoing laser resurfacing, a study was conducted. Five hundred (500) milligrams per 100 milliliters (0.5 grams percent) of Ester-C® brand vitamin C was combined with the aqueous composition including silica network particles of the present invention. After application to laser resurfacing patients to reduce the discomfort of laser resurfacing, seven of eight patients were evaluated by digital photography and color analysis, and a 25% reduction in time to healing to preoperative color occurred with the vitamin C product having the aqueous composition including silica network particles of the present invention compared to standard post-laser treatment. There was evidence of an overall improvement in hydration in these patients and an improvement in the delivery of vitamin C to the skin. There was also a 25% reduction in redness in these patients.

EXAMPLE 5

Additional studies were performed on fibroblast cultures in vitro and showed a statistically significant reduction in metalloproteases and in the activity of metalloprotease I and II. When the aqueous composition including silica network particles of the present invention was applied to the culture. This finding has significant importance in disease processes in which an imbalance of metalloproteases and tissue inhibitors of metalloproteases, exists.

EXAMPLE 6

A study was performed on radiation therapy patients having damaged skin. It was determined from the study that no harmful effects occurred on the damaged skin of these patients when the damaged skin was contacted with the aqueous composition including silica network particles of the present invention.

From Examples 1–6, it can be seen that the aqueous composition including silica network particles of the present invention provides a base that is a superior vehicle in transporting water and other compositions into the skin. The composition of the present invention exchanges water more readily with healthy or damaged skin than does bulk water and enhances the effectiveness of a wide variety of cosmetic preparations as gauged by clinical trials. It is evident that agents incorporating the aqueous composition of the present invention lead to better skin hydration in the majority of the subjects compared to similar agents without the aqueous composition of the present invention. The composition also provides improved skin hydration and reduces fine wrinkles and enhances skin tone when incorporated into a skin care composition. When incorporated into a body care composition, the composition of the present invention is effective in enhancing the quality of the skin and thus is: (1) a skin treating compound, (2) an enhancer of other skin treatment agents, (3) a carrier, and (4) a cosmetic additive.

The aqueous composition of the present invention can effectively deliver other antioxidants beyond the stratum corneum. Products including the aqueous composition of the present invention have been used in a mist, gel, lotion and cream base, each form demonstrating its effectiveness. Products including the aqueous composition of the present invention are well tolerated and hydrate the skin successfully by allowing moisture to penetrate the skin. This is in contrast to prior compositions in which hydrophobic materials are transported into the skin to block moisture loss.

There has also been successful demonstration of a formulation having the aqueous composition of the present invention as a hair conditioner. Studies indicate increased absorption through the hair and increased strength of hair strands.

It should be understood that the methods and apparatuses described above are only exemplary and do not limit the scope of the invention, and that various modifications could be made by those skilled in the art that would fall under the scope of the invention. To apprise the public of the scope of this invention, the following claims are made.

What is claimed is:

1. A method of generating silica network particles in water, the method comprising the steps of:
    (a) dissolving sodium silicate in water to form a solution;
    (b) agitating the solution;
    (c) thereafter circulating the solution through an alternating magnetic field greater than the earth's magnetic field;
    (d) thereafter agitating the solution;
    (e) thereafter circulating the solution through the alternating magnetic field; and
    (f) repeating steps (d) and (e) a plurality of times until silica network particles are formed in the solution,
wherein step (c) comprises circulating the solution through a helical coil around vertical columns of evenly spaced magnets creating an alternating magnetic field.

2. The method of claim 1 wherein:
    step (a) comprises dissolving sodium metasilicate pentahydrate in water to form the solution.

3. The method of claim 1 wherein:
    step (a) comprises dissolving sodium silicate in water to form the solution, the solution having from about 100 parts per million silica to about 500 parts per million silica.

4. The method of claim 1 wherein:
    step (b) comprises shearing the solution with a blade.

5. The method of claim 1 wherein:
    step (b) comprises agitating the solution in an open-air mixing chamber until the solution absorbs sufficient carbon dioxide to lower the pH to between about 9.5 and about 10.5.

6. The method of claim 1 wherein:
    step (f) comprises repeating steps (d) and (e) a plurality of times until the solution absorbs sufficient carbon dioxide to lower the pH to between about 8.5 and about 9.5.

7. The method of claim 1 wherein:
    step (d) comprises shearing the solution with a blade in an open-air mixing vessel.

8. The method of claim 1 wherein:
    step (f) comprises repeating steps (d) and (e) a plurality of times until silica network particles are formed in the solution, the silica network particles comprising main particles having a particle size greater than a first particle size and bridging particles having a particle size less than the first particle size, the bridging particles forming chains between adjacent main particles.

9. The method of claim 1 wherein:
    step (e) comprises circulating an aerated portion of the solution through a helical coil around vertical columns of evenly spaced magnets creating an alternating magnetic field.

10. The method of claim 1 wherein:
    step (f) comprises repeating steps (d) and (e) a plurality of times until silica network particles are formed in the solution, the silica network particles having a particle size greater than or equal to 1000 nanometers.

11. The method of claim 1 wherein:
step (f) comprises repeating steps (d) and (e) a plurality of times until silica network particles are formed in the solution, the silica network particles having a particle size greater than or equal to 3000 nanometers, and the silica network particles comprising main particles and bridging particles forming chains between adjacent main particles.

12. The method of claim 1 wherein:
step (f) comprises repeating steps (d) and (e) a plurality of times until silica network particles are formed in the solution, the silica network particles comprising main particles and bridging particles forming chains between adjacent main particles, the main particles and the bridging particles having a substantially spheroid shape.

13. The method of claim 1 wherein:
step (e) comprises repeating steps (d) and (e) a plurality of times until silica network particles are formed in the solution and the solution is capable of wetting a hydrophobic substrate more than pure liquid water.

14. The method of claim 1 wherein:
step (f) comprises repeating steps (d) and (e) a plurality of times until silica network particles are formed in the solution and the solution has a carbonate concentration of about 4 to about 8 millimoles per liter.

15. An apparatus for generating silica network particles in water, the apparatus comprising:
a mixing vessel for holding a silicate solution;
a mixer for agitating the silicate solution, the mixer being located In the mixing vessel;
a magnetic field generating unit including a plurality of spaced apart magnets and tubing coiled around the magnets; and
a solution circulation system for circulating the silicate solution from the mixing vessel through the tubing and back to the mixing vessel.

16. The apparatus of claim 15 wherein:
the solution circulation system comprises
a pump having an inlet and an outlet,
a first conduit in fluid communication with the inlet of the pump and the mixing vessel;
a second conduit in fluid communication with the outlet of the pump and an intake end of the tubing; and
a third conduit in fluid communication with an output end of the tubing and the mixing vessel.

17. The apparatus of claim 15 wherein:
the magnets are arranged such that the poles of adjacent magnets face in opposite directions.

18. The apparatus of claim 15 wherein:
the magnetic field strength is approximately 1000 Gauss at a pole face of each magnet.

19. The apparatus of claim 15 wherein:
the mixer comprises a motor, a shaft mechanically coupled to the motor, and a shearing blade attached to the shaft for agitating the silicate solution.

20. The apparatus of claim 15 wherein:
the magnetic field generating unit further comprises a cylindrical drum made from a ferromagnetic material, and
the magnets are positioned along an inner surface of the cylindrical drum and the tubing encircles an outer surface of the cylindrical drum.

21. The apparatus of claim 20 wherein:
the magnets are vertical columns evenly spaced along the inner surface of the cylindrical drum.

22. The apparatus of claim 21 wherein:
the magnetic field generating unit further comprises a plurality of non-magnetic columns positioned between the magnets.

23. The apparatus of claim 21 wherein:
the tubing of the magnetic field generating unit is coiled around the magnets such that the direction of solution flow is substantially perpendicular to the vertical columns of magnets.

24. The apparatus of claim 20 wherein:
the magnetic field generating unit further comprises
an outer cylindrical drum made from a ferromagnetic material, and
a second group of magnets positioned along an inner surface of the outer cylindrical drum and outside the tubing.

25. A method of generating silica network particles in water, the method comprising the steps of:
(a) dissolving sodium silicate in water to form a solution;
(b) agitating the solution;
(c) thereafter circulating the solution through an alternating magnetic field greater than the earth's magnetic field;
(d) thereafter agitating the solution;
(e) thereafter circulating the solution through the alternating magnetic field; and
(f) repeating steps (d) and (e) a plurality of times until silica network particles are formed in the solution,
wherein step (b) comprises agitating the solution in an open-air mixing chamber until the solution absorbs sufficient carbon dioxide to lower the pH to between about 9.5 and about 10.5.

26. A method of generating silica network particles in water, the method comprising the steps of:
(a) dissolving sodium silicate in water to form a solution;
(b) agitating the solution,
(c) thereafter circulating the solution through an alternating magnetic field greater than the earth's magnetic field;
(d) thereafter agitating the solution;
(e) thereafter circulating the solution through the alternating magnetic field; and
(f) repeating steps (d) and (e) a plurality of times until silica network particles are formed in the solution,
wherein step (f) comprises repeating steps (d) and (e) a plurality of times until the solution absorbs sufficient carbon dioxide to lower the pH to between about 8.5 and about 9.6.

27. A method of generating silica network particles in water, the method comprising the steps of:
(a) dissolving sodium silicate in water to form a solution;
(b) agitating the solution;
(c) thereafter circulating the solution through an alternating magnetic field greater than the earth's magnetic field;
(d) thereafter agitating the solution;
(e) thereafter circulating the solution through the alternating magnetic field; and
(f) repeating steps (d) and (e) a plurality of times until silica network particles are formed in the solution,
wherein step (f) comprises repeating steps (d) and (e) a plurality of times until silica network particles are formed in the solution, the silica network particles having a particle size greater than or equal to 1000 nanometers.

28. A method of generating silica network particles in water, the method comprising the steps of:
  (a) dissolving sodium silicate in water to form a solution;
  (b) agitating the solution;
  (c) thereafter circulating the solution through an alternating magnetic field greater than the earth's magnetic field;
  (d) thereafter agitating the solution;
  (e) thereafter circulating the solution through the alternating magnetic field; and
  (f) repeating steps (d) and (e) a plurality of times until silica network particles are formed in the solution,
wherein step (f) comprises repeating steps (d) and (e) a plurality of times until silica network particles are formed in the solution, the silica network particles having a particle size greater than or equal to 3000 nanometers, and the silica network particles comprising main particles and bridging particles forming chains between adjacent main particles.

29. A method of generating silica network particles in water, the method comprising the steps of:
  (a) dissolving sodium silicate in water to form a solution;
  (b) agitating the solution;
  (c) thereafter circulating the solution through an alternating magnetic field greater than the earth's magnetic field;
  (d) thereafter agitating the solution;
  (e) thereafter circulating the solution through the alternating magnetic field; and
  (f) repeating steps (d) and (e) a plurality of times until silica network particles are formed in the solution,
wherein step (f) comprises repeating steps (d) and (e) a plurality of times until silica network particles are formed in the solution and the solution has a carbonate concentration of about 4 to about 8 millimoles per liter.

* * * * *